United States Patent
Allison et al.

(10) Patent No.: US 12,320,637 B2
(45) Date of Patent: Jun. 3, 2025

(54) DEVICE AND METHOD TO MONITOR A PERSON

(71) Applicant: Bob Barker Company, Inc., Fuquay-Varina, NC (US)

(72) Inventors: Gerrad Stephen Allison, Angier, NC (US); Jessica Ann Schwendeman, Apex, NC (US)

(73) Assignee: BOB BARKER COMPANY, INC., Fuquay-Varina, NC (US)

( * ) Notice: Subject to any disclaimer, the term of this patent is extended or adjusted under 35 U.S.C. 154(b) by 69 days.

(21) Appl. No.: 18/087,017

(22) Filed: Dec. 22, 2022

(65) Prior Publication Data

US 2023/0204337 A1    Jun. 29, 2023

Related U.S. Application Data (60) Provisional application No. 63/294,188, filed on Dec. 28, 2021.

(51) Int. Cl.
*G01B 7/16* (2006.01)

(52) U.S. Cl.
CPC ...................................... *G01B 7/18* (2013.01)

(58) Field of Classification Search
CPC .. G01B 7/18; G08B 21/0453; A61B 5/02055; A61B 5/1113; A61B 2562/164
See application file for complete search history.

(56) References Cited

U.S. PATENT DOCUMENTS

| | | | |
|---|---|---|---|
| 2007/0166831 A1* | 7/2007 | Watkins | G01N 27/20 436/149 |
| 2015/0250420 A1* | 9/2015 | Longinotti-Buitoni | A61B 5/1135 600/534 |
| 2015/0379857 A1* | 12/2015 | Larose | G08B 21/185 340/652 |
| 2018/0190102 A1* | 7/2018 | Lui | G08B 21/20 |
| 2018/0271409 A1* | 9/2018 | Gong | A61B 5/1118 |
| 2018/0364850 A1* | 12/2018 | Vosgueritchian | G06F 3/0416 |
| 2022/0061699 A1* | 3/2022 | LaBove | A61B 5/1116 |

* cited by examiner

*Primary Examiner* — Jermele M Hollington
*Assistant Examiner* — Zannatul Ferdous
(74) *Attorney, Agent, or Firm* — COATS & BENNETT, PLLC (57) ABSTRACT

A sensing device to monitor a person. The sensing device includes a sensing strip and control unit that are attached to an article. The sensing strip has one or more electrical properties that change when the shape of the sensing strip changes. The control unit receives data from the sensing strip and transmits one or more of the data and processed data to a remote node.

16 Claims, 6 Drawing Sheets

DEVICE AND METHOD TO MONITOR A PERSON

RELATED APPLICATIONS

This claims priority to U.S. Provisional Application No. 63/294,188, filed Dec. 28, 2021, the disclosure of which is incorporated herein by reference in its entirety.

BACKGROUND

Institutional facilities such as but not limited to jails, juvenile detention centers, and prisons monitor the status of their inmates. The monitoring can include but is not limited to monitoring the inmate to determine breathing and movement. For example, the facility can monitor the status while an inmate is sleeping to ensure they are not in need of medical assistance. The monitoring can also include that an article in the inmate's possession is not being used as a weapon or for other improper use.

The monitoring equipment should be designed to prevent its use as a weapon for an inmate to injure themselves, another inmate, or a guard. This includes preventing the entirety of the equipment from being fashioned into a weapon. This also includes preventing one or more pieces of the equipment from being removed and used as a weapon.

SUMMARY

One aspect is directed to a sensing device to monitor a person in an institutional facility. The sensing device comprises an article that is flexible, a sensing strip attached to the article with the sensing strip being flexible to change shape with a change in a shape of the article, and a control unit connected to the sensing strip with the control unit comprising control circuitry and communication circuitry. The control unit is configured to determine a change in one or more electrical properties of the sensing strip due to the change in the shape of the sensing strip. The control unit is further configured to transmit a signal to a remote node in response to determining the change in one or more of the electrical properties.

In another aspect, the article comprises multiple layers with the sensing strip and the control unit positioned between two of the layers to visually obscure the sensing strip and the control unit.

In another aspect, a power source is connected to the article and configured to provide electrical power to the sensing strip and the control unit.

In another aspect, the one or more electrical properties comprises electrical resistance.

In another aspect, the sensing strip comprises conductive ink that has been applied to the article.

In another aspect, the sensing strip comprises a polymeric foil impregnated with carbon black.

In another aspect, the article is a band with a length that is greater than a width and is configured to be attached to one of a wrist and an ankle of the person.

In another aspect, the sensing strip is a first sensing strip and further comprising a second sensing strip attached to the article with the second sensing strip being flexible to change shape with changes in the shape of the article and with the second sensing strip spaced apart on the article from the first sensing strip.

In another aspect, the article is a mattress.

One aspect is directed to a sensing device to monitor a person in an institutional facility. The sensing device comprises an article, and a sensor attached to the article and comprising a sensing strip with an elongated shape attached to the article. The sensor is configured to determine a change in one or more electrical properties of the sensing strip due to the person using the article and to transmit a signal to a remote node after determining the change in one or more of the electrical properties.

In another aspect, the sensor is configured to transmit the signal to the remote node in response to detecting the change in the one or more electrical properties.

In another aspect, the sensor further comprises a control unit connected to the sensing strip and to the article with the control unit comprising control circuitry and communication circuitry.

In another aspect, the article is configured to be worn by the person and comprises a first layer and a second layer with the sensor positioned between the first layer and the second layer to be visually obscured when the article is worn by the person.

In another aspect, the sensor is configured to transmit the signal through radio-frequency identification (RFID).

In another aspect, the sensing strip comprises one of conductive ink and a polymeric foil impregnated with carbon black.

In another aspect, the article is a mattress and the sensor is configured to determine the change in one or more electrical properties of the sensing strip in response to the person laying on the mattress.

One aspect is directed to a method of using a sensing device to monitor a person within an institutional facility. The method comprises: monitoring one or more electrical properties of a sensing strip that is attached to an article; while the person is using an article, detecting a change in the one or more electrical properties due to movement of the person; and transmitting a signal to a remote node indicating the one or more electrical properties.

In another aspect, the method further comprises detecting the change in the one or more electrical properties due to a change in a shape of the article.

In another aspect, the method further comprises transmitting the signal to the remote node in response to detecting the change in the one or more electrical properties.

In another aspect, detecting the change in the one or more electrical properties comprises detecting a change in an electrical resistance of the sensing strip.

One aspect is directed to a sensing device to monitor a person in an institutional facility. The sensing device comprises an article, a sensing strip attached to the article, and a control unit connected to the sensing strip with the control unit comprising control circuitry and communication circuitry. The control unit is configured to determine a change in one or more electrical properties of the sensing strip. The control unit is further configured to transmit a signal to a remote node in response to determining the change in one or more of the electrical properties.

In another aspect, a power source is mounted to the article and configured to provide electrical power to the sensing strip and the control unit.

In another aspect, the sensing strip is configured to change the one or more electrical properties based on applied pressure.

In another aspect, the one or more electrical properties comprises electrical resistance.

In another aspect, the sensing strip comprises conductive ink.

In another aspect, the sensing strip is thinner than the article.

In another aspect, the article is a band with a length that is greater than a width and configured to be attached to one or a wrist and an ankle of the person.

In another aspect, the sensing strip comprises a polymeric foil impregnated with carbon black.

In another aspect, the second strip comprises VELOSTAT material.

In another aspect, the sensing strip is a conductive ink.

In another aspect, the sensing strip and the article are flexible.

In another aspect, the sensing strip and the article flex an equal amount.

One aspect is directed to a sensing device to monitor a person in an institutional facility. The sensing device comprises an article, a sensing strip attached to the article, and a control unit connected to the sensing strip with the control unit comprising control circuitry and communication circuitry. The control unit is configured to transmit to a remote node data regarding one or more electrical properties of the sensing strip.

In another aspect, the control unit is further configured to transmit a signal to a remote node in response to determining the change in one or more of the electrical properties.

In another aspect, a power source is mounted to the article and configured to provide electrical power to the sensing strip and the control unit.

In another aspect, the sensing strip is configured to change the one or more electrical properties based on applied pressure.

In another aspect, the one or more electrical properties comprises electrical resistance.

In another aspect, the sensing strip comprises conductive ink.

In another aspect, the article is a band with a length that is greater than a width and configured to be attached to one or a wrist and an ankle of the person.

In another aspect, the sensing strip comprises a polymeric foil impregnated with carbon black.

In another aspect, the second strip comprises VELOSTAT material.

In another aspect, the sensing strip is a conductive ink.

In another aspect, the sensing strip and the article are flexible.

In another aspect, the sensing strip and the article flex an equal amount.

One aspect is directed to a method of monitoring a person that is using a sensing device. The method comprises: detecting one or more electrical properties of the sensing device while the detecting device is being used by the person with the detecting device comprising a sensing strip; detecting a change in one or more of the electrical properties of the sensing device; and transmitting a signal to a remote node indicating the change in the one or more electrical properties.

In another aspect, the method further comprises changing a shape of the sensing strip and in response detecting the change in the one or more electrical properties.

In another aspect, the method further comprises transmitting the signal to the remote node in response to detecting the change in the one or more electrical properties.

The various aspects of the various embodiments may be used alone or in any combination, as is desired.

DETAILED DESCRIPTION

Figure 1:
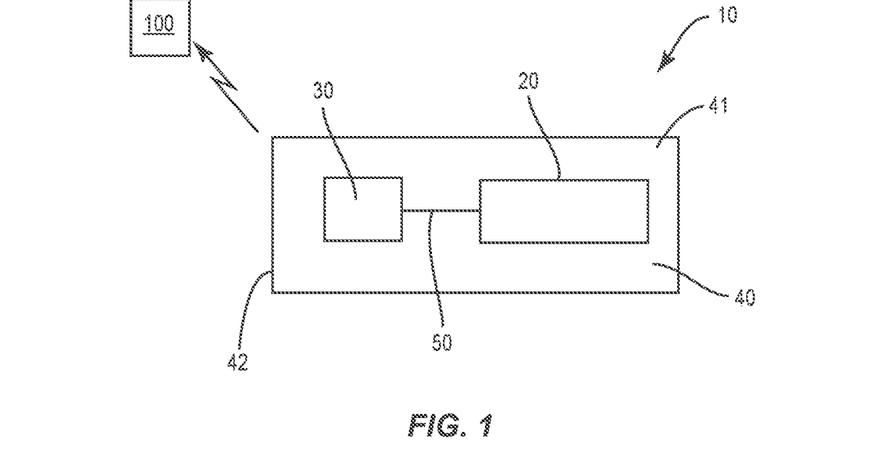
FIG. 1 is a schematic view of a sensing device configured to communicate with a remote node.

FIG. 1 schematically illustrates a sensing device 10 to monitor a person. The sensing device 10 includes a sensing strip 20 and control unit 30 that are attached to an article 40. The sensing strip 20 has one or more electrical properties that change when the shape of the sensing strip 20 changes. The change in shape can occur when the sensing strip changes shape or when pressure is applied to the sensing strip 20. The control unit 30 receives data from the sensing strip 20 and transmits one or more of the data and processed data to a remote node 100.

The sensing device 10 can be incorporated into a variety of different articles 40. One type of article 40 is a garment that is worn by the person. Examples include but are not limited to a band for positioning on arm, leg, head, or waist, a top, a bottom, a shirt, a sweatshirt, pants, jacket, sock, and hat. Another type of article 40 is an item that is handled by the person. Examples include but are not limited to a towel, a sheet, and a blanket. Another example is a mattress.

In one example, the article 40 is flexible. The flexible article 40 changes shape when used by the person. Examples include but are not limited to a shirt or a towel that changes shape when used by the person, and a mattress that deforms when supporting a person. In another example, the article 40 is relatively rigid to maintain its shape when used by the person. The article 40 can be constructed from a variety of different materials. Examples include but are not limited to textile products made into a fabric or cloth and constructed from various natural or synthetic materials, leather, plastic, rubber, and combinations thereof.

The sensing strip 20 is attached to the article 40. In one example, the sensing strip 20 is attached to one of an inner face 41 or an outer face 42 of the article 40. The inner face 41 is positioned towards and may contact against the person when the article is worn. The outer face 42 is positioned away from the person. In another example, the sensing strip 20 is incorporated into the article 40 and/or positioned within an interior of the article 40 between the inner and outer faces 41, 42. The sensing strip 20 can be attached to the article 40 in different manners. Examples include but are not limited to being applied to the article 40 as a liquid and secured upon drying; sewn onto the article 40; and positioned within an interior of the article between the inner and outer faces 41, 42.

The sensing strip 20 is electrically conductive and exhibits one or more electrical properties when operatively connected to a power source 34. The electrical properties can include but are not limited to voltage, current, and resistance, as well as one or more combinations and/or derivations of these electrical properties. In some examples, the one or more of the electrical properties change due to changes in the shape of sensing strip 20. Changes in the shape can be caused by various forces being applied, such as when pressure applied to the sensing strip 20 and/or forces due to the article being worn/used by the person. In another example, the sensing strip 20 is configured to detect electrical impulses that are emitted from the person and that cause changes to one or more of the electrical properties. In one example, the sensing strip 20 is configured to detect current and/or voltage that are received from the person.

In one example, the sensing strip 20 is configured to detect changes in a single electrical property (e.g., just resistance, just voltage). In other examples, the sensing strip 20 is configured to detect changes in two or more electrical properties. In one example, the sensing strip 20 is configured to detect a change in the one or more electrical properties due to a single cause (e.g., just by change in shape, just through detecting electrical impulses). Other examples include the sensing strip 20 configured to detect changes to or more of the electrical properties. In one example, the device 20 includes two or more sensing strips 20. Each sensing strip 20 is configured to detect a change in a different electrical property.

The sensing strip 20 can include different constructions. One example includes a conductive ink that includes graphite or other conductive material that is contained within ink. Another example includes the sensing strip 20 being VELOSTAT material that is made of a polymeric foil that is impregnated with carbon black thus making it electrically conductive. In one example, the sensing strip 20 is a coating that is applied to the article 40 in a liquid form. The coating dries to a solid form and adheres to the article 40. In another example, the sensing strip 20 is attached to the article 40 by various physical connectors such as but not limited to fasteners, thread, and adhesive.

Figure 2:
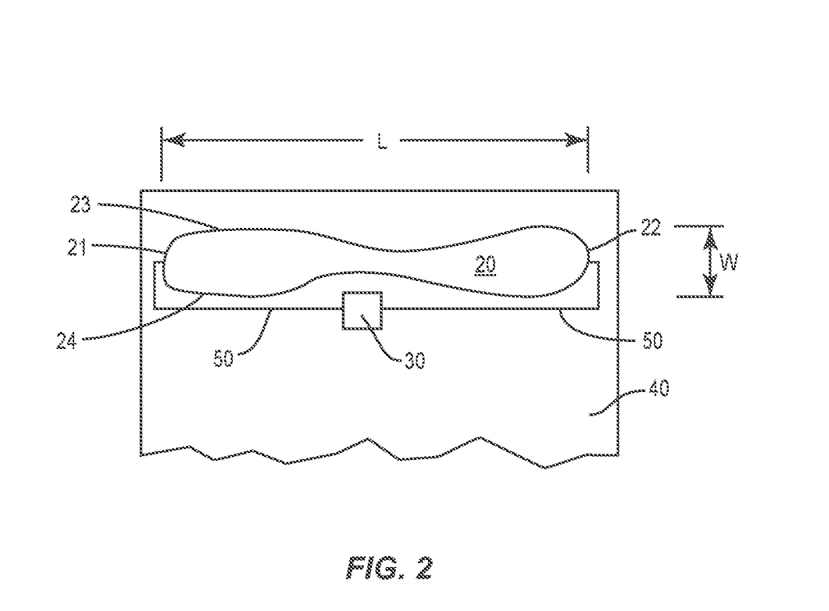
FIG. 2 is a schematic view of a sensing device.

The sensing strip 20 can include various shapes and sizes. Shapes include but are not limited to rectangular, polygonal, circular, and oval. FIG. 2 includes an example with the sensing strip 20 having a substantially hourglass shape. The sensing strip 20 includes a length L measured between opposing ends 21, 22, and a width W measured between opposing sides 23, 24.

In one example, the sensing strip 20 is flexible and the shape changes due to the changing shape of the article 40 to which it is attached. The change results in a change in one or both of the length L and width W. The change in shape can occur along the entire length and/or width, or one or more limited sections of the length and/or width.

Figure 3:
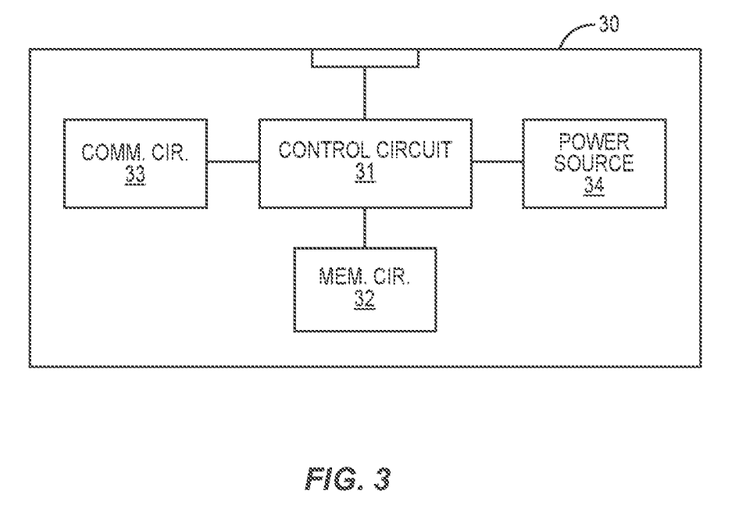
FIG. 3 is a schematic view of a control unit.

The control unit 30 is connected to the sensing strip 20. FIG. 3 schematically illustrates a control unit 30 that includes a control circuit 31 and a memory circuit 32. The control circuit 31 controls operation of the sensing device 10 according to program instructions stored in the memory circuit 32. The control circuit 31 can include one or more circuits, microcontrol units, microprocessors, hardware, or a combination thereof. Memory circuit 32 includes a non-transitory computer readable storage medium storing program instructions, such as a computer program product, that configures the control circuit 31 to implement one or more of the techniques discussed herein. Memory circuit 32 can include various memory devices such as, for example, read-only memory, and flash memory. Memory circuit 32 can be a separate component as illustrated in FIG. 3 or can be incorporated with the control circuit 31. Alternatively, the control circuit 31 can omit the memory circuit 32, e.g., according to at least some examples in which the control circuit 31 is dedicated and non-programmable.

The control unit 30 is further configured to provide for communication functionality with the remote node 100. The communication can include outgoing communications to remote node 100. The communication can also include incoming communications from the remote node 100. A communications circuit 33 provides for the communication functionality. The communication circuit 33 can include a WLAN interface configured to communicate with a local area network, e.g., via a wireless access point. An exemplary WLAN interface could operate according to the 802.11 family of standards, which is commonly known as a WiFi interface. The communication circuit 33 can further include a personal area network interface, such as a Bluetooth interface. The communication circuit 33 can also include a Near Field Communication interface that provides for short-range wireless connectivity technology that uses magnetic field induction to permit the sensing device 10 to share information with the remote node 100. The communication circuit 33 can also be configured to operate using RFID interrogation.

In one example as illustrated in FIG. 3, the communications circuit 33 is incorporated into the control unit 30. In another example, the communications circuit 33 is a separate system that is operatively connected to and controlled by the control unit 30.

The control unit 30 can communicate with the remote node 100 at various time intervals. One example includes communication on a regular timed basis (e.g., every 10 seconds, every minute, every 5 minutes). Another example includes communicating in response to detecting a change in one or more of the electrical properties. In another example, the control unit 30 communicates the detected data upon receiving a request from the remote node 100.

A power source 34 provides power to the control unit 30 and the sensing strip 20. The power source 34 can include various configurations such as batteries. FIG. 3 includes the power source 34 incorporated with the control unit 30. In another example, the power source 34 can be separate from the control unit 30 and configured to provide power to the control unit 30. As illustrated in FIG. 2, one or more leads 50 extend between and connect the power source 34 to the sensing strip 20.

Figure 4:
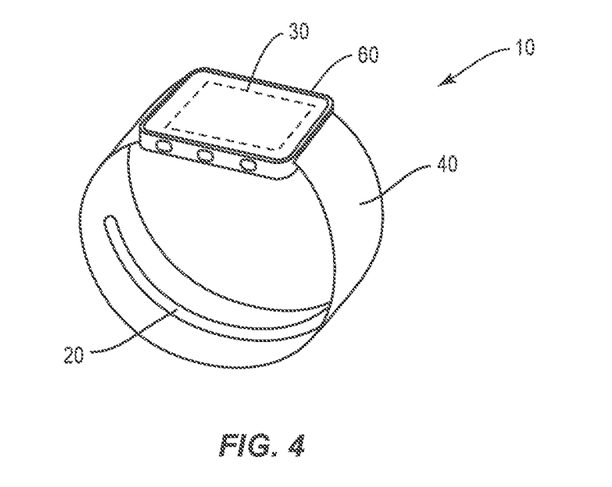
FIG. 4 is a perspective view of a sensing device configured as a band.

The sensing device 10 can have a variety of different configurations. FIG. 4 illustrates an example of a sensing device 10 formed as a band configured to attached to a person's wrist or ankle. The article 40 has an elongated length and relatively narrow width. The sensing strip 20 extends along a section of the length of the band 40 and is connected to the control unit 30. The control unit 30 is positioned within a housing 60 that extends around and protects the control unit 30. The housing 60 is attached to the band.

Figure 5:
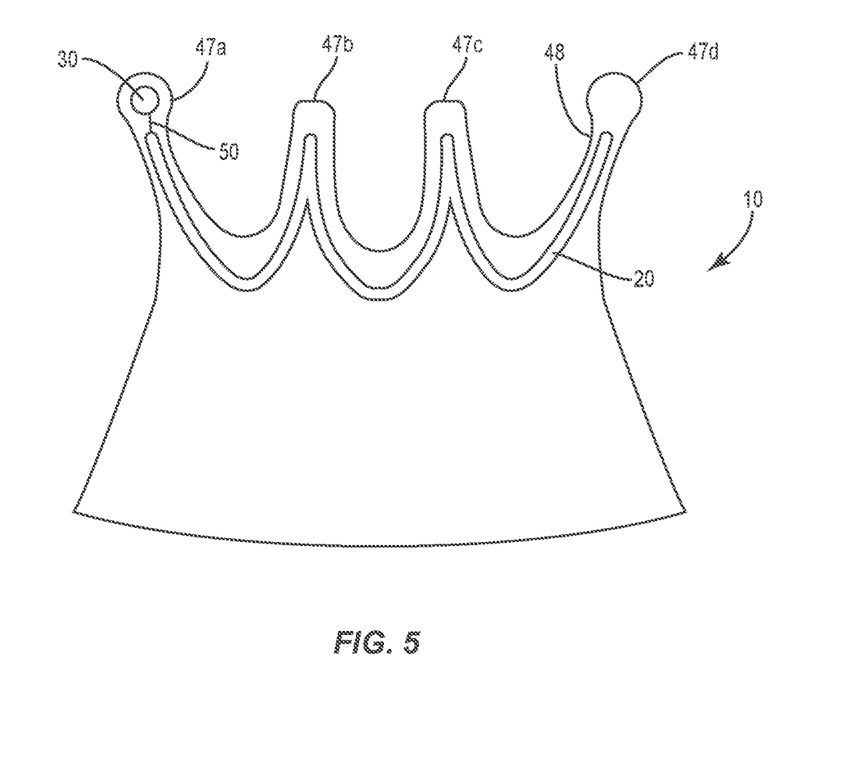
FIG. 5 is a side view of a sensing device configured as a smock with the smock in a flat orientation prior to use by a person.

FIG. 5 illustrates another example of a sensing device 10. The article 40 is a smock that includes an upper edge 48 with straps 47*a*, 47*b*, 47*c*, 47*d*. FIG. 5 illustrates the smock in a flat orientation when not being worn by a person. During use, the smock is wrapped around the person with the straps 47*a*, 47*b* connecting together to form a first arm opening and straps 47*c*, 47*d* connecting together to form a second arm opening. A neck opening is formed between straps 47*b*, 47*c*. The sensing strip 20 is attached to the smock and extends along the upper edge 48. In one example, the sensing strip 20 is positioned at the upper edge 48, with another example having the sensing strip 20 positioned inward away from the upper edge 48. The control unit 30 is attached to the smock in proximity to the sensing strip 20 and connected through one or more leads 50.

Figure 6:
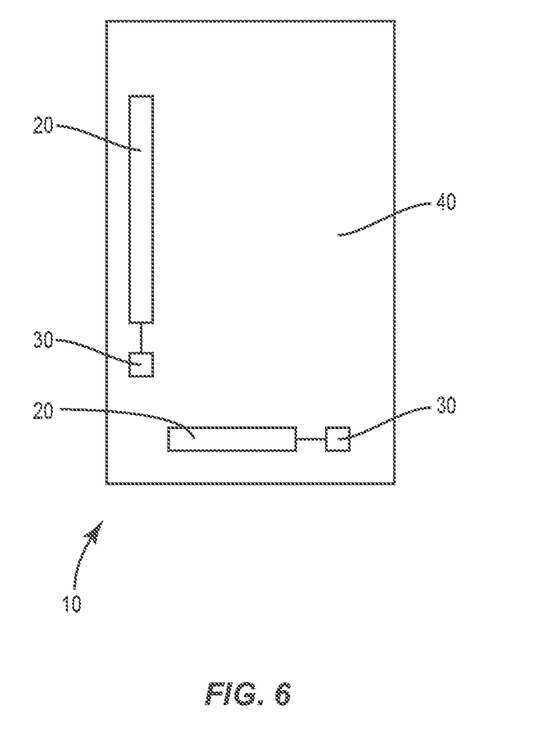
FIG. 6 is a side view of a sensing device configured as a towel or blanket.

FIG. 6 illustrates an example of a sensing device 10 in which the article 40 is a towel or sheet. The sensing strip 20 extends along a section of the article 40.

In one example, the sensing device 10 includes a single sensing strip 20. In another example, the sensing device 10 includes two or more sensing strips 20. The different sensing strips 20 can be positioned at different locations on the article. FIG. 6 includes an example with a pair of sensing strips 20 positioned at different locations on the article 40. The multiple sensing strips 20 can each have their own dedicated control unit 30 as illustrated in FIG. 6. In another example, a control unit 30 is connected to and receives data from two or more sensing strips 20. In one example, the different sensing strips 20 are configured with one or more different electrical properties.

The sensing strip 20 exhibits one or more electrical properties when connected to the power source 34. When the sensing device 10 is being used by the person, the one or more electrical properties change and the change is detected by the control unit 30. Thus the person is able to be monitored based on the detected changes (or lack of changes).

In one example, the change in the one or more electrical properties occurs when there is a change to sensing strip 20. In one example, the change 20 is an amount of pressure that is applied to the sensing strip 20. Additionally or alternatively, the one or more electrical properties can change when the sensing strip 20 changes shape. For example, a person wearing a sensing device 10 while sleeping can cause a change in the one or more electrical properties during movement in their sleep. In one example, this movement can be tossing and turning during sleep. This can also include just the heartbeat of the user causing a change to the sensing strip 20.

Figure 7:
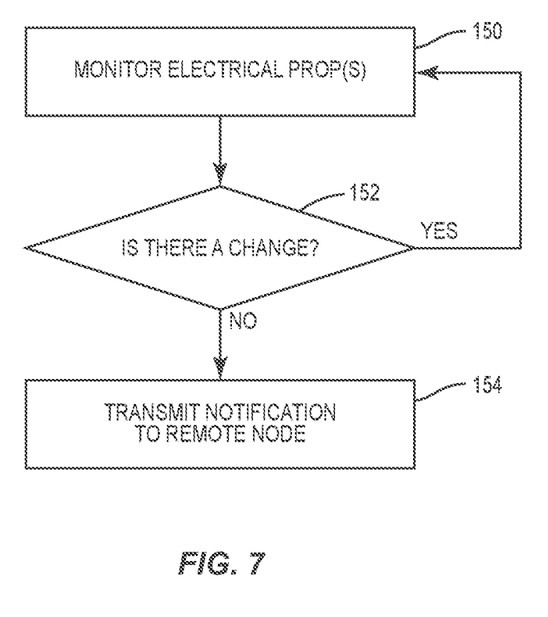
FIG. 7 is a method of monitoring a person using a sensing device.

FIG. 7 illustrates a method of monitoring a person that is using a sensing device 10. In one specific example, the sensing device 10 is a garment that is being worn by the user. In another example, the sensing device 10 is an article such as a blanket that is being handled by the user. During use, the control unit 30 monitors the one or more electrical properties of the sensing strip 20 (block 150). If there is a change (block 152), the control unit 30 continues to monitor the person. The change in the one or more electrical properties indicates one or more of the person moving, breathing, having a heartbeat, or otherwise active and therefore not in need of attention. If there is no change, the control unit 30 transmits a notification to the remote node 100 (block 154).

The determination of whether there is a change in the one or more electrical properties can occur over various time periods. One example tracking heartbeat may have a first time interval in which a change is expected to be detected (e.g., 3 seconds). Another example monitors the breathing cycle and has a different time interval (e.g., 8 seconds). Another example monitors movement of the person and has a longer time interval (e.g., 5 minutes). The expected time interval can be set as needed for the specific context of use. The amount of change in the one or more electrical properties that causes a notification to be transmitted can also be set as necessary.

The sensing device 10 can be used to determine if the article 40 is being improperly used by a person. For example, whether a garment or a towel is being used as a rope to hurt themselves or another, or when the article is tied into a knot to form a weapon or mode to escape. This monitoring can also determine if the article 40 has been ripped along the sensing strip 20. When the article 40 is being used as expected, the sensing strip 20 has a first level of the one or more electrical properties. When the article 40 is being used as a weapon (e.g., twisted into a rope), the sensing strip has a second level of the one or more electrical properties.

Figure 8:
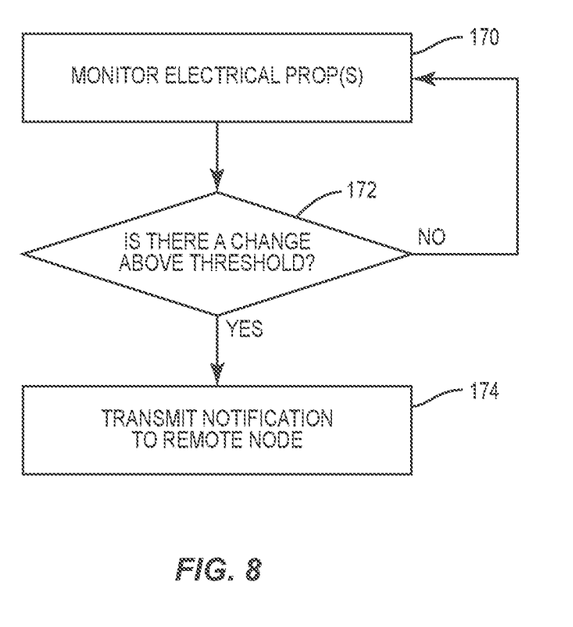
FIG. 8 is a method of monitoring a person using a sensing device.

FIG. 8 illustrates a method of monitoring a person to determine how the article 40 is being used. The control unit 30 monitors the one or more electrical properties of the sensing strip 20 (block 170). The one or more electrical properties are at a first level when the article 40 is being used properly. The control unit 30 determines whether there is a change above a predetermined amount (block 172). If the level is not above the amount, the control unit 30 continues the monitoring. If the level is above the amount indicating that the article 40 is being used improperly, a notification is transmitted to the remote node 100 (block 174).

In the examples described above, the control unit 30 monitors the one or more electrical properties and determines if there is a change. In another example, the control unit 30 simply receives the data from the sensing strip 20 and transmits the data to the remote node 100. Processing of the data is performed at the remote node 100 that is positioned away from the sensing device 10.

In one example, the sensing strip 20 and/or the control unit 30 are hidden on the article 40. In one example, the article comprises multiple layers, such as a garment having inner and outer layers. The sensing strip 20 and/or control unit 30 are positioned between the layers. This positioning hides these components and prevents and/or reduces the likelihood that the person will try to remove them from the article 40 or otherwise try to use them as a weapon. In another example with the article 40 being a mattress, the sensing strip 20 and/or control unit 30 are positioned within the mattress below an outer layer. Again, this positioning hides these components from the person.

The examples described include the article 40 as part of the sensing device 10. In another example, the sensing device 10 does not include the article 40, but just the sensing strip 20 and control unit 30. This sensing device 10 can then be used as necessary.

In another example, the control unit 30 is not attached to the article 40 but is positioned remotely away from the article 40 and sensing strip 20. The control unit 30 can obtain the data through radio-frequency identification (RFID). The control unit 30 includes a transponder, receiver, and transmitter. The control unit 30 is triggered by an interrogation pulse from a reader device in the area and transmits data detected by the sensing strip 20.

In one example, the control unit 30 monitors just for changes in resistance.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

By the term "substantially" with reference to amounts or measurement values, it is meant that the recited characteristic, parameter, or value need not be achieved exactly. Rather, deviations or variations, including, for example, tolerances, measurement error, measurement accuracy limitations, and other factors known to those skilled in the art, may occur in amounts that do not preclude the effect that the characteristic was intended to provide.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential properties of the invention. The present embodiments are, therefore, to be considered in all respects as illustrative and not restrictive.

What is claimed is:

1. A sensing device to monitor a person in an institutional facility, the sensing device comprising:
   an article that is flexible;
   a sensing strip attached to the article, the sensing strip comprising just a single layer and being flexible to change shape with a change in a shape of the article;
   a control unit connected to the sensing strip with the control unit comprising control circuitry and communication circuitry;
   wherein the control unit is configured to determine a change in one or more electrical properties of the sensing strip due to the change in the shape of the sensing strip; and
   wherein the control unit is further configured to transmit a signal to a remote node in response to determining the change in one or more of the electrical properties.

2. The sensing device of claim 1, wherein the article comprises multiple layers with the sensing strip and the control unit positioned between two of the layers to visually obscure the sensing strip and the control unit.

3. The sensing device of claim 1, further comprising a power source connected to the article and configured to provide electrical power to the sensing strip and the control unit.

4. The sensing device of claim 1, wherein the one or more electrical properties comprises electrical resistance.

5. The sensing device of claim 1, wherein the sensing strip is just a conductive ink that has been applied to the article.

6. The sensing device of claim 1, wherein the sensing strip is just a polymeric foil impregnated with carbon black.

7. The sensing device of claim 1, wherein the article is a band with a length that is greater than a width and is configured to be attached to one of a wrist and an ankle of the person.

8. The sensing device of claim 1, wherein the sensing strip is a first sensing strip and further comprising a second sensing strip attached to the article with the second sensing strip being flexible to change shape with changes in the shape of the article and with the second sensing strip spaced apart on the article from the first sensing strip.

9. The sensing device of claim 1, wherein the article is a mattress.

10. A sensing device to monitor a person in an institutional facility, the sensing device comprising:
    an article; and
    a sensor attached to the article and comprising a sensing strip with an elongated shape attached to the article, the sensing strip comprising just a single layer, the sensor configured to determine a change in one or more electrical properties of the sensing strip due to the person using the article and to transmit a signal to a remote node after determining the change in one or more of the electrical properties.

11. The sensing device of claim 10, wherein the sensor is configured to transmit the signal to the remote node in response to detecting the change in the one or more electrical properties.

12. The sensing device of claim 10, wherein the sensor further comprises a control unit connected to the sensing strip and to the article, the control unit comprising control circuitry and communication circuitry.

13. The sensing device of claim 10, wherein the article is configured to be worn by the person and comprises a first layer and a second layer, the sensor positioned between the first layer and the second layer to be visually obscured when the article is worn by the person.

14. The sensing device of claim 10, wherein the sensor is configured to transmit the signal through radio-frequency identification (RFID).

15. The sensing device of claim 10, wherein the sensing strip comprises one of conductive ink and a polymeric foil impregnated with carbon black.

16. The sensing device of claim 10, wherein the article is a mattress and the sensor is configured to determine the change in one or more electrical properties of the sensing strip in response to the person laying on the mattress.

* * * * *